(12) United States Patent
Mapes et al.

(10) Patent No.: US 8,048,093 B2
(45) Date of Patent: Nov. 1, 2011

(54) TEXTURED BALLOONS

(75) Inventors: Kenneth W. Mapes, Temecula, CA (US); Christopher G. Kunis, Escondido, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1710 days.

(21) Appl. No.: 10/741,694

(22) Filed: Dec. 19, 2003

(65) Prior Publication Data
US 2005/0137615 A1  Jun. 23, 2005

(51) Int. Cl.
*A61B 17/22* (2006.01)
(52) U.S. Cl. ..................................................... 606/159
(58) Field of Classification Search .............. 606/159, 606/170, 194–198, 108; 604/103.06–103.08; 264/400
See application file for complete search history.

(56) References Cited

U.S. PATENT DOCUMENTS

| | | | |
|---|---|---|---|
| 3,141,912 A | 7/1964 | Goldman et al. | |
| 3,635,223 A | 1/1972 | Klieman | |
| 4,106,723 A * | 8/1978 | Couture | 242/118.3 |
| 4,273,128 A | 6/1981 | Lary | |
| 4,444,186 A * | 4/1984 | Wolvek et al. | 606/194 |
| 4,490,421 A | 12/1984 | Levy | |
| 4,681,110 A | 7/1987 | Wiktor | |
| 4,696,667 A | 9/1987 | Masch | |
| 4,702,252 A | 10/1987 | Brooks et al. | |
| 4,723,549 A | 2/1988 | Wholey et al. | |
| 4,728,319 A | 3/1988 | Masch | |
| 4,781,186 A | 11/1988 | Simpson et al. | |
| 4,787,388 A | 11/1988 | Hofmann | |
| 4,867,157 A | 9/1989 | McGurk-Burleson et al. | |
| 4,886,061 A | 12/1989 | Fischell et al. | |
| 4,887,613 A | 12/1989 | Farr et al. | |
| 4,896,669 A | 1/1990 | Bhate et al. | |
| 4,909,781 A | 3/1990 | Husted | |
| 4,913,701 A * | 4/1990 | Tower | 604/103 |
| 4,927,412 A * | 5/1990 | Menasche | 604/103.08 |
| 4,950,277 A | 8/1990 | Farr | |
| 4,952,357 A | 8/1990 | Euteneuer | |
| 4,986,807 A | 1/1991 | Farr | |
| 5,009,659 A | 4/1991 | Hamlin et al. | |
| 5,030,201 A | 7/1991 | Palestrant | |
| 5,053,044 A | 10/1991 | Mueller et al. | |
| 5,055,024 A * | 10/1991 | Jackowski et al. | 425/140 |
| 5,074,871 A | 12/1991 | Groshong | |
| 5,156,610 A | 10/1992 | Reger | |
| 5,176,693 A | 1/1993 | Pannek, Jr. | |
| 5,178,625 A | 1/1993 | Groshong | |
| 5,192,291 A | 3/1993 | Pannek, Jr. | |
| 5,196,024 A * | 3/1993 | Barath | 606/159 |
| 5,209,799 A * | 5/1993 | Vigil | 156/156 |
| 5,211,683 A * | 5/1993 | Maginot | 128/898 |
| 5,224,945 A | 7/1993 | Pannek, Jr. | |

(Continued)

*Primary Examiner* — Elizabeth Houston
(74) *Attorney, Agent, or Firm* — Seager Tufte Wickhem LLC

(57) ABSTRACT

A cutting balloon for use in PTCA and PTA procedures and methods for manufacturing cutting balloons are disclosed. One or more surfaces of the cutting balloon are formed with a non-smooth surface texture to improve adhesion between cutting blades and the inflatable balloon, to improve traction between the cutting balloon and the arterial wall, or to prevent inadvertent balloon perforation by a cutting blade. Textures, which can include a knurling texture and a nodular texture can be formed on the inflatable balloon surface directly using laser ablation. Alternatively, the texture can be formed on a mold surface used to mold the inflatable balloon from a parison. Mold surfaces can be textured using a laser photolithography process, sandblasting or a high-speed tool such as a diamond saw.

8 Claims, 4 Drawing Sheets

U.S. PATENT DOCUMENTS

| | | | |
|---|---|---|---|
| 5,226,909 A | 7/1993 | Evans et al. | |
| 5,282,484 A | 2/1994 | Reger | |
| 5,312,427 A | 5/1994 | Shturman | |
| 5,320,634 A * | 6/1994 | Vigil et al. | 606/159 |
| 5,334,146 A | 8/1994 | Ozasa | |
| 5,336,234 A | 8/1994 | Vigil et al. | |
| 5,372,601 A | 12/1994 | Lary | |
| 5,478,426 A * | 12/1995 | Wiler et al. | 156/272.8 |
| 5,494,029 A * | 2/1996 | Lane et al. | 128/207.15 |
| 5,556,405 A | 9/1996 | Lary | |
| 5,556,408 A | 9/1996 | Farhat | |
| 5,616,149 A | 4/1997 | Barath | |
| 5,697,944 A | 12/1997 | Lary | |
| 5,713,913 A | 2/1998 | Lary et al. | |
| 5,721,023 A * | 2/1998 | Ostapchenko | 428/35.2 |
| 5,728,123 A | 3/1998 | Lemelson et al. | |
| 5,746,745 A * | 5/1998 | Abele et al. | 623/1.11 |
| 5,792,158 A | 8/1998 | Lary | |
| 5,797,935 A * | 8/1998 | Barath | 606/159 |
| 5,833,657 A | 11/1998 | Reinhardt et al. | |
| 5,919,200 A | 7/1999 | Stambaugh et al. | |
| 5,954,740 A * | 9/1999 | Ravenscroft et al. | 606/194 |
| 6,027,514 A | 2/2000 | Stine et al. | |
| 6,096,054 A | 8/2000 | Wyzgala et al. | |
| 6,117,153 A | 9/2000 | Lary et al. | |
| 6,129,706 A * | 10/2000 | Janacek | 604/103.08 |
| 6,161,353 A * | 12/2000 | Negola et al. | 52/453 |
| 6,176,698 B1 * | 1/2001 | Grantz et al. | 425/470 |
| 6,197,013 B1 * | 3/2001 | Reed et al. | 604/509 |
| 6,258,099 B1 * | 7/2001 | Mareiro et al. | 606/108 |
| 6,258,108 B1 | 7/2001 | Lary | |
| 6,264,633 B1 * | 7/2001 | Knorig | 604/102.01 |
| 6,306,151 B1 | 10/2001 | Lary | |
| 6,416,523 B1 | 7/2002 | Lafontaine | |
| 6,416,526 B1 | 7/2002 | Wyzgala et al. | |
| 6,428,539 B1 | 8/2002 | Baxter et al. | |
| 6,445,676 B1 * | 9/2002 | Fujii et al. | 369/281 |
| 6,500,145 B1 * | 12/2002 | Bicakci et al. | 604/96.01 |
| 6,632,231 B2 * | 10/2003 | Radisch, Jr. | 606/159 |
| 6,645,422 B2 * | 11/2003 | Jung et al. | 264/530 |
| 6,736,841 B2 * | 5/2004 | Musbach et al. | 623/1.11 |
| 6,780,497 B1 * | 8/2004 | Walter | 428/311.51 |
| 6,786,889 B1 * | 9/2004 | Musbach et al. | 604/103.08 |
| 6,942,680 B2 * | 9/2005 | Grayzel et al. | 606/194 |
| 7,153,315 B2 * | 12/2006 | Miller | 606/159 |
| 7,494,497 B2 * | 2/2009 | Weber | 606/159 |
| 2004/0026359 A1 * | 2/2004 | Dufresne et al. | 216/8 |
| 2004/0086674 A1 * | 5/2004 | Holman | 428/36.9 |
| 2005/0119678 A1 * | 6/2005 | O'Brien et al. | 606/159 |

* cited by examiner

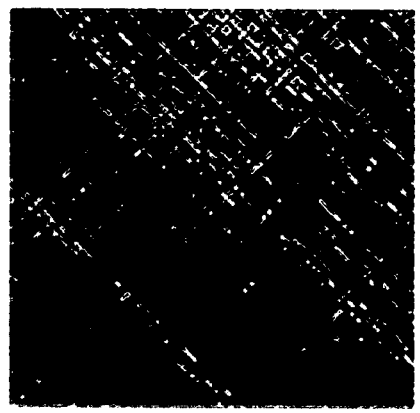
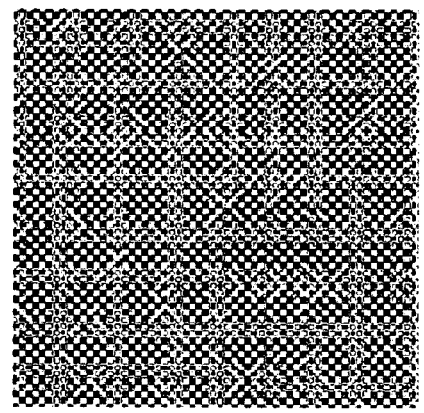
Fig. 6            Fig. 7
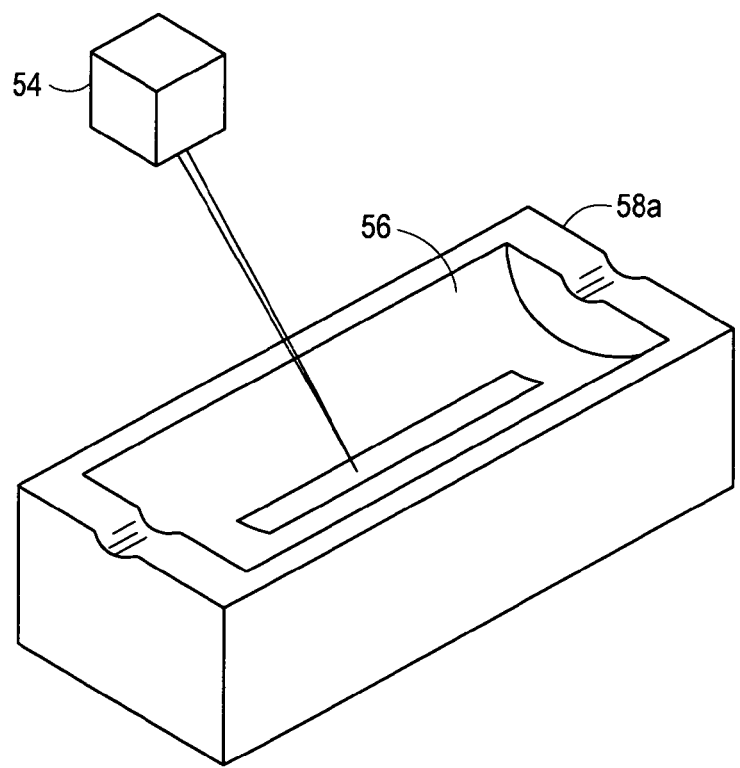
Fig. 8

TEXTURED BALLOONS

FIELD OF THE INVENTION

The present invention pertains generally to medical devices. More particularly, the present invention pertains to balloon catheters. The present invention is particularly, but not exclusively, useful as a cutting balloon for the revascularization of coronary and peripheral vessels.

BACKGROUND OF THE INVENTION

Although conventional percutaneous, transluminal, coronary angioplasty (PTCA) and percutaneous, transluminal, angioplasty (PTA) procedures have been somewhat effective in treating coronary artery disease, incising devices, such as cutting balloons, are currently viewed by many as the next generation treatment option for the revascularization of both coronary and peripheral vessels. The cutting balloon mechanism is unique in that the balloon pressure is distributed over one or more blades (i.e. microtomes). The blade(s) function as stress concentrators and cut initiators in PTCA and PTA procedures. Importantly, PTCA and PTA procedures that employ cutting balloons for this purpose have been proven to minimize vessel recoil, lessen vessel injury and lower the rate of restenosis, as compared to conventional PTCA and PTA procedures.

In the past, typical cutting balloons have been prepared by first encapsulating a portion of an incising element, such as a metal cutting blade, in a blade pad. The blade pad is then adhesively bonded to the smooth outer surface of an inflatable balloon. In some instances, however, this type of bond between the blade pad and the balloon has been somewhat inadequate due to the inability of the adhesive to bond to the smooth surfaces of the balloon and pad. In particular, relatively long blades require a strong bond due to the differential expansion rate of the metal blade and the flexible balloon material. An inadequate bond is especially troublesome in light of the grave consequences that can result if a blade pad de-bonds from the balloon while the balloon is located in a sensitive area of the patient. For example, a de-bonding of a blade pad from an inflatable balloon in or near the heart would in most cases require immediate, high-risk open-heart surgery to remedy.

The cutting blades used in cutting balloons are extremely sharp (e.g. three to five times sharper than a conventional scalpel). In the absence of suitable precautions, the sharp blades can tear, cut or perforate the thin, fragile inflatable balloon during assembly of the cutting balloon, handling or during clinical use. In a worst case, a balloon perforation or tear can result in an unsuccessful PTCA/PTA procedure and the loss of inflation fluid into the patient's vasculature.

In a typical PTCA and PTA procedure, a cutting balloon is advanced through the vasculature of a patient with the balloon in a deflated configuration. The balloon is then precisely positioned across a lesion in the vessel that is to be treated. Once the balloon has been properly positioned, fluid is infused into the balloon to expand the balloon into an inflated configuration. As the balloon expands, the blades cut into the lesion and the surface of the balloon presses against the lesion, dilating the lesion to increase the effective diameter of the vessel. In turn, the portion of the lesion that is in contact with the balloon produces reactive forces on the balloon. For a lesion that is lubricious, the reactive forces may overcome the frictional forces between the balloon and the lesion. If this happens, slippage can occur between the balloon and the lesion resulting in unwanted movement of the balloon relative to the lesion. For instance, the reactive forces can cause the balloon to shoot forward or backward through the vessel in a longitudinal direction (i.e., "the watermelon seed effect"). This unwanted movement is often deleterious to the PTCA and PTA procedure because dilation and cutting may not occur at the desired location in the vessel. Thus, unless unwanted movement of the balloon relative to the lesion can be prevented, the effectiveness of the PTCA and PTA procedure may be significantly reduced.

In light of the above, it is an object of the present invention to provide cutting balloons and methods for their manufacture having cutting blades that are strongly bonded to the surface of an inflatable balloon. It is another object of the present invention to provide methods for forming surface textures on one or more cutting balloon surfaces to promote adhesion between the cutting blades and the inflatable balloon, to improve traction between the cutting balloon and the arterial wall, or to prevent inflatable balloon perforation by a cutting blade. Yet another object of the present invention is to provide cutting balloons and methods for their manufacture that are easy to use, relatively simple to implement, and comparatively cost effective.

SUMMARY OF THE INVENTION

The present invention is directed to incising devices, such as cutting balloons, for use in vessel revascularization and methods for manufacturing incising devices. A typical incising device includes an inflatable balloon, one or more elongated incising elements, and one or more mounting pads (e.g. blade pads). For the present invention, the incising elements can include, but are not limited to, cutting blades, round wires and hardened polymers. Each mounting pad is bonded to the inflatable balloon and is provided to hold a respective incising element. For the present invention, one or more surfaces of the incising device are formed with a non-smooth surface texture to enhance the performance of the incising device. The non-smooth surface texture can include, but is not limited to, a knurling texture, a nodular texture, or a texture having spiral, sinuous or random indentations.

In a first aspect of the present invention, a portion of the outer surface of the inflatable balloon is formed with non-smooth surface texture such as a knurling texture. A mounting pad is then adhesively bonded to the textured surface of the inflatable balloon. The textured surface provides more surface area than a similarly sized smooth surface, and accordingly, a stronger bond is obtained between the inflatable balloon and the mounting pad. Alternatively, or in addition to forming a portion of the inflatable balloon with a non-smooth surface texture, a bonding surface on the mounting pad can be formed with a non-smooth surface texture to increase the bond strength between the inflatable balloon and the mounting pad.

In another aspect of the present invention, non-bonding surfaces of the inflatable balloon (i.e. surfaces that remain exposed after the mounting pad(s) have been bonded to the inflatable balloon) are formed with a non-smooth surface texture. In one embodiment, the exposed surface of the inflatable balloon is formed with a plurality of nodules that prevent the incising elements from puncturing the inflatable balloon. In another embodiment, an exposed portion of the working section of the inflatable balloon is textured to promote traction between the inflatable balloon surface and the affected arterial wall to anchor the incising device at the treatment site during a balloon inflation. Other applications for the texture include balloon identification and the use of a spiral pattern in stripped balloons to increase flexibility with a minimal effect on burst pressure.

In another aspect of the invention, a method for manufacturing an incising device includes the step of providing an inflatable balloon having an inner surface for surrounding an inflation volume and an opposed outer surface having at least one surface portion formed with a non-smooth surface texture. The method further includes the step of mounting at least one incising element on the outer surface of the inflatable balloon.

In a first embodiment of the manufacturing method, the step of providing an inflatable balloon having at least one surface portion formed with a non-smooth surface texture is accomplished by providing a mold having a smooth mold surface and forming a non-smooth surface texture on at least a portion of the mold surface. A parison is then positioned in the mold and expanded onto the mold surface to produce the inflatable balloon having the non-smooth surface texture. The non-smooth surface texture can be formed on the mold surface using one of several procedures. In a first procedure, a non-smooth surface texture is formed on the mold surface using a laser photolithography procedure. Alternatively, a non-smooth surface texture can be formed on the mold surface by selectively sandblasting portions of said mold surface or the texture can be formed using a diamond saw.

In another embodiment of the manufacturing method, the step of providing an inflatable balloon having at least one surface portion formed with a non-smooth surface texture is accomplished by providing an inflatable balloon having a smooth outer surface. Next, a laser is used to ablate the smooth outer surface of the balloon to form the non-smooth surface texture.

To mount an incising element on the outer surface of the inflatable balloon, the manufacturing method may include the steps of encapsulating a portion of the incising element in a mounting pad and adhesively bonding the mounting pad to the surface portion of the inflatable balloon formed with a non-smooth surface texture. In one implementation, the mounting pad is first formed with a smooth bonding surface. Next, a laser is used to ablate the bonding surface to form a non-smooth surface texture thereon. The textured bonding surface is then adhesively bonded to the surface portion of the inflatable balloon that is formed with a non-smooth surface texture.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6 is a representative illustration of a surface having a knurled surface texture formed thereon;

FIG. 7 is a representative illustration of a surface having a nodular surface texture formed thereon;

FIG. 8 is a is a simplified schematic view of a laser source activating a photoresist on the surface of a mold to form a non-smooth surface texture thereon;

DESCRIPTION OF THE PREFERRED EMBODIMENTS

Figure 1:
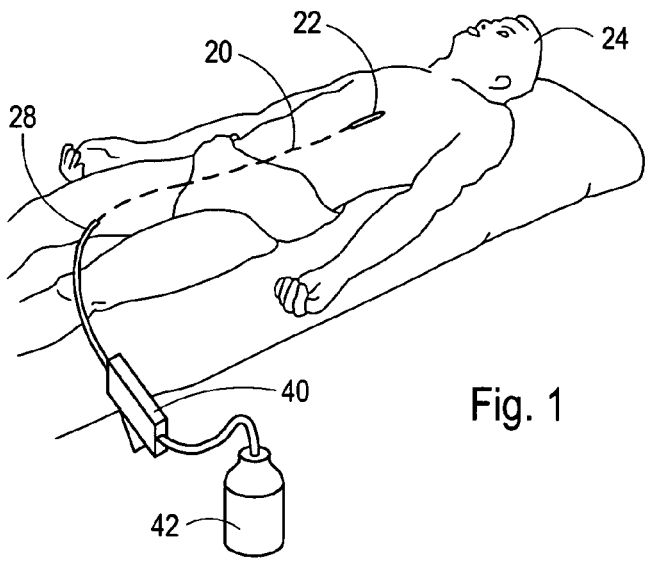
FIG. 1 is a simplified, perspective view of a catheter having a cutting balloon operationally positioned in the upper body of a patient.

Referring initially to FIG. 1, a catheter 20 having an incising device, which in this case is a cutting balloon 22, is shown for performing a medical procedure at an internal treatment site of a patient 24. More specifically, the catheter 20 is shown positioned to treat a lesion in an upper body artery. Although the catheter 20 is capable of performing a medical procedure in an upper body artery such as a coronary artery, those skilled in the pertinent art will recognize that the use of the catheter 20 as herein described is not limited to use in a specific artery, but, instead can be used in vascular conduits and other ductal systems throughout the human body.

Figure 2:
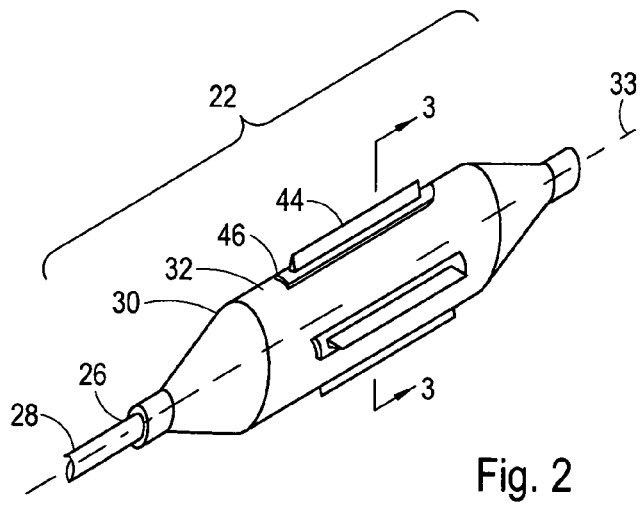
FIG. 2 is an enlarged, perspective view of a cutting balloon.
Figure 3:
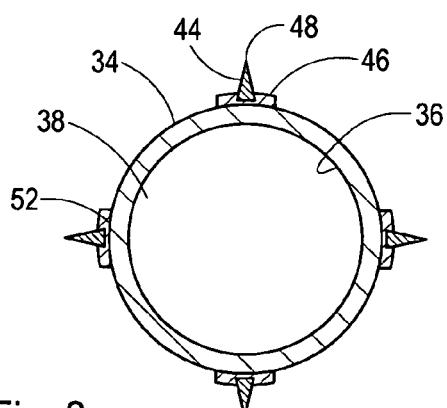
FIG. 3 is a cross-sectional view of the cutting balloon shown in FIG. 2 as seen along line 3-3 in FIG. 2.

Referring now to FIG. 2, the distal portion of the catheter 20 is shown to include a cutting balloon 22 that is attached to the distal end 26 of an inflation tube 28. FIG. 2 further shows that the cutting balloon 22 can include an inflatable balloon 30 that typically includes a cylindrical shaped working section 32 that defines an axis 33. Typically, the inflatable balloon 30 is made of a relatively flexible polymeric material such as, but not limited to, polyethylene terephthalate (PET). As best seen in FIG. 3, the inflatable balloon 30 can be characterized as having an outer surface 34 and an opposed inner surface 36 that surrounds an inflation volume 38, which in turn, can be infused with a medical grade fluid to expand the inflatable balloon 30. More specifically, as shown in FIG. 1, a fluid pump 40 can be activated to pump a medical grade fluid from a fluid reservoir 42 and through the inflation tube 28 to expand the inflatable balloon 30.

Figure 4:
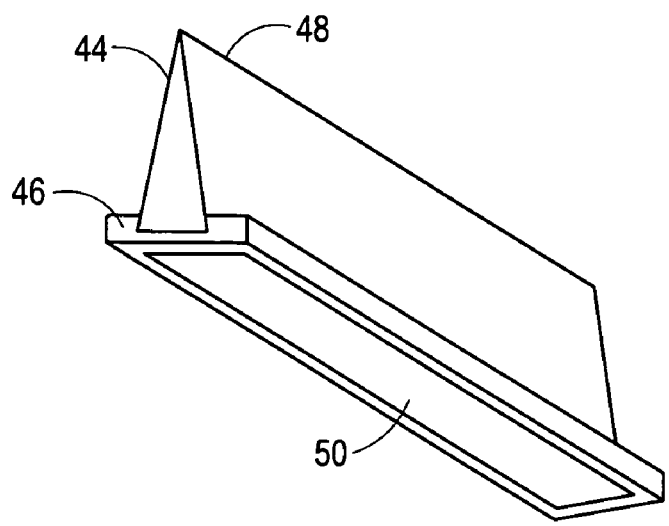
FIG. 4 is a simplified, perspective view of a blade encapsulated in a blade pad.

Cross-referencing FIGS. 2 and 3, it can be seen that the cutting balloon 22 further includes a plurality of elongated incising elements, which for the embodiment shown are cutting blades 44. In alternate embodiments, round wires or hardened polymers are used as incising elements. For the embodiment shown, four longitudinally aligned blades 44 are uniformly distributed around the circumference of the working section 32 of the inflatable balloon 30. Typically, each blade 44 is made of a medical grade metal such as stainless steel. As best seen in FIG. 3, a portion of each blade 44 is encapsulated in a respective blade pad 46, thereby affixing the blade 44 to the respective blade pad 46. Typically, each blade pad 46 is made of a relatively flexible polymeric material such as polyurethane. From the blade pad 46, each blade 44 extends radially to a sharp edge 48. Cross-referencing FIGS. 3 and 4, it can be seen that each blade pad 46 includes a bonding surface 50 that is adhesively bonded to a bonding surface 52 on the outer surface 34 of the inflatable balloon 30 using an adhesive such as polyurethane.

Figure 5:
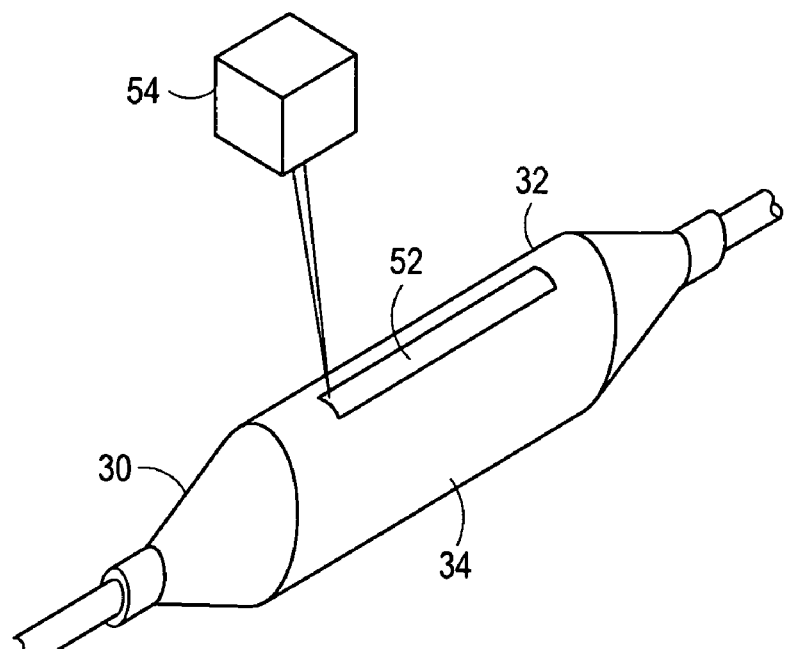
FIG. 5 is a simplified schematic view of a laser source ablating the surface of an inflatable balloon to form a non-smooth surface texture thereon.

In a first embodiment of the catheter 20, one or both of the bonding surfaces 50, 52 are formed with a non-smooth surface texture to increase the strength of the adhesive bond between the blade pad 46 and the outer surface 34 of the inflatable balloon 30. FIG. 5 illustrates a first manufacturing method for forming a non-smooth surface texture on a bonding surface 50, 52, which in this case is a longitudinally aligned strip located on the working section 32 of the inflatable balloon 30. FIG. 5 illustrates that a laser source 54 can be used to ablate balloon material on the outer surface 34 of the inflatable balloon 30. The laser source 54 can also be used to ablate blade pad material on the bonding surface 50 of a blade pad 46.

The laser source 54 may include a direct writing KrF excimer laser operating at 248 nm or a HeCd laser operating at 442 nm, that generates a laser beam. In addition, the laser source 54 may include optics to both focus the beam on the outer surface 34 and scan the beam along the outer surface 34 of the inflatable balloon 30. Using this technique, a knurling texture as shown in FIG. 6 can be produced on the curved outer surface 34 having a first set of parallel grooves and a second set of parallel grooves that are aligned at an angle relative to the first set of grooves. Grooves having an approximate width in the range of 5-10 μm can be used to increase the effective surface area of the bonding surface by approximately 50-100%. In some cases, a stencil, mask or photoresist material can be used to limit the ablation to selected areas on the outer surface 34.

The laser source 54 can be used to ablate portions (or all) of the outer surface 34 with a nodule texture, such as the texture shown in FIG. 7, to improve traction between the cutting balloon 22 and the arterial wall, or to prevent perforation of the inflatable balloon 30 by a cutting blade 44 during assembly, handling or clinical use.

FIG. 8 illustrates an alternative manufacturing method for forming a non-smooth surface texture on the outer surface 34 of the inflatable balloon 30. In this manufacturing method, laser photolithography is first used to form a texture, such as the knurling texture shown in FIG. 6, on the initially smooth surface 56 of a mold half 58a. This technique is similar to the technique used in the fabrication of integrated circuits. A photomask is placed on the surface 56 and laser light from laser source 54 is used to selectly activate the photoresist to create the desired texture. The laser source 54 may include a direct writing KrF excimer laser operating at 248 nm or a HeCd laser operating at 442 nm, that generates a laser beam. In addition, the laser source 54 may include optics to both focus the beam on the surface 56 and scan the beam along the surface 56 of the mold half 58a. Where laser light strikes the photoresistive material, its composition is changed. Photoresistive material not affected by light is washed off. Finally, the surface 56 is exposed to an etching solution such as potassium hydroxide that dissolves portions of the surface 56 not protected by the photoresistive material to create the desired texture pattern on the surface 56 of the mold half 58a. Alternatively, a non-smooth surface texture can be formed on the mold surface 56 by selectively sandblasting portions of said mold surface 56 or the texture can be formed using a high speed tool such as a diamond saw.

Figure 9:
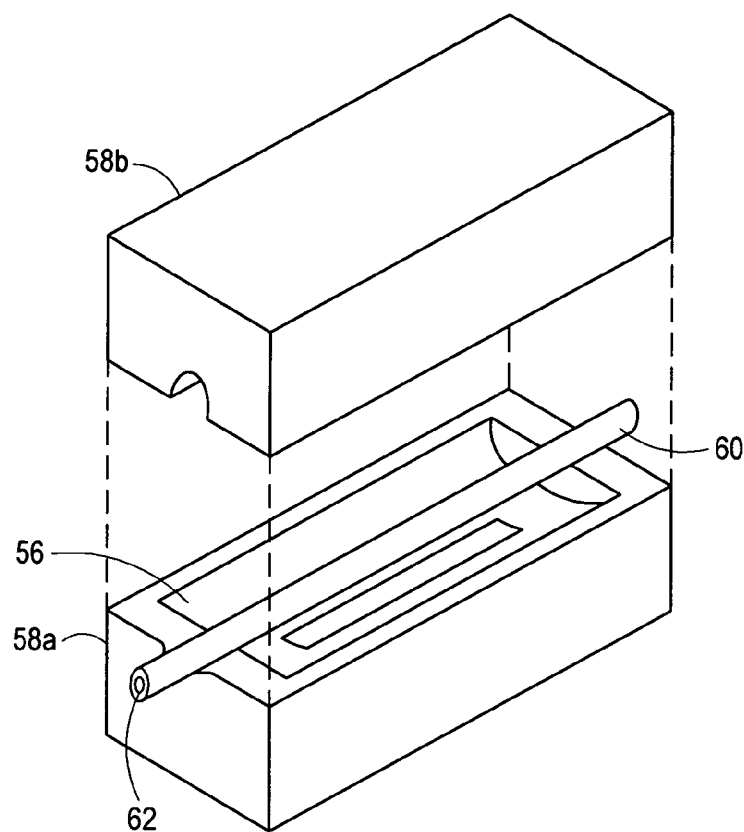
FIG. 9 is a simplified schematic view of a parison positioned for expansion in a mold having a non-smooth surface texture formed thereon.

As shown in FIG. 9, once the desired texture pattern has been formed on the surface 56 of the mold half 58a, a parison, which in this case is a hollow tube 60 made of a polymeric material such as polyethylene terephthalate (PET), is heated to a working temperature and placed in the cavity of the two-piece mold 58a,b. With the tube 60 positioned in the mold cavity and the mold 58a,b closed, the lumen 62 of the tube 60 is pressurized to radially expand the tube 60 onto the mold surface 56. It is to be appreciated that the mold half 58a will transfer (e.g. stamp) the non-smooth surface texture onto portions of the tube 60. The result is an inflatable balloon 30 having a non-smooth surface texture on selected portions (or all) of its outer surface 34. Using this mold transfer technique, a knurling texture as shown in FIG. 6 can be produced on the curved outer surface 34 having a first set of parallel grooves and a second set of parallel grooves that are aligned at an angle relative to the first set of grooves. Grooves having an approximate width in the range of 5-10 μm can be used to increase the effective surface area of the bonding surface by approximately 50-100%.

The laser source 54 shown in FIG. 8 can be used to form a nodule texture on the surface 56 of the mold half 58a, such as the texture shown in FIG. 7. The nodular texture is then transferred to the outer surface 34 of the inflatable balloon 30 during radial expansion of a parison, as described above. The nodular texture can be used to improve traction between the cutting balloon 22 and the arterial wall, or to prevent perforation of the inflatable balloon 30 by a cutting blade 44 during assembly, handling or clinical use.

Figure 10:
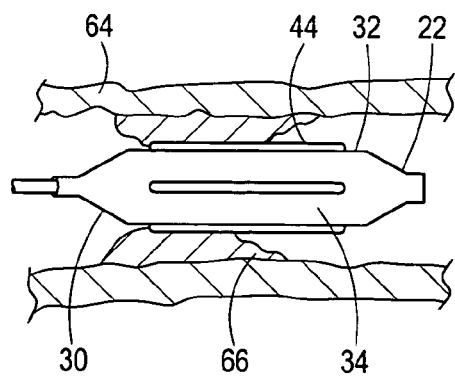
FIG. 10 is an enlarged view of a cutting balloon positioned at a treatment site.

A typical use of the catheter 20 can best be appreciated with cross-reference to FIGS. 1 and 10. In a typical use, the cutting balloon 22 is deflated and inserted into the vasculature of the patient 24 using a peripheral artery, such as the femoral artery, for access. Once in the vasculature, the cutting balloon 22 is advanced to a treatment site such as the treatment site shown in FIG. 10, which illustrates a coronary artery 64 that is constricted by a lesion 66. With the working section of the balloon 32 positioned across to the lesion 66, the fluid pump 40 is activated to pass a fluid through the inflation tube 28 and into the inflatable balloon 30. As the inflatable balloon 30 expands, one or more of the blades 44 contact the lesion 66 and function as stress concentrators and cut initiators. In addition, a non-smooth surface texture on the outer surface 34 of the inflatable balloon 30 engages the lesion 66, anchoring the cutting balloon 22 at the treatment site, preventing longitudinal movement of the balloon 30 during further inflation of the inflatable balloon 30. Thus, the inflatable balloon 30 can be further inflated without longitudinal balloon movement allowing the cutting balloon 22 to cut and compact the lesion 66 and dilate artery 64.

While the particular textured balloons and methods of manufacture as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A method for manufacturing an incising device, said method comprising the steps of:
   providing an inflatable balloon having an inner surface for surrounding an inflation volume and an opposed outer surface, said inflatable balloon being formed by a layer of a polymeric material extending from the inner surface to the outer surface of the balloon;
   ablating a portion of the polymeric material from the outer surface of the balloon along an inflatable body portion of said balloon with a laser to form a knurled bonding surface having a knurled surface texture defined by a first set of parallel grooves and a second set of parallel grooves aligned at an angle to the first set of parallel grooves; and
   mounting at least one incising element on said knurled bonding surface of said outer surface of said balloon.

2. A method as recited in claim 1 wherein said incising element is a cutting blade and said step of mounting at least one incising element on said outer surface of said balloon is accomplished by:
   encapsulating a portion of said cutting blade in a blade pad; and adhesively bonding said blade pad to said knurled bonding surface of said outer surface of said balloon.

3. A method as recited in claim 1 wherein said incising element is a cutting blade and said step of mounting at least one incising element on said outer surface of said balloon is accomplished by:
encapsulating a portion of said cutting blade in a blade pad, said blade pad formed with a smooth bonding surface;
laser ablating said smooth bonding surface of said blade pad to form said non-smooth surface texture on said bonding surface of said blade pad; and
adhesively bonding said bonding surface of said blade pad to said knurled bonding surface of said outer surface of said balloon.

4. A cutting balloon comprising:
a cutting blade;
a blade pad for holding said cutting blade, said blade pad having a bonding surface;
an inflatable balloon having an inner surface for surrounding an inflation volume and an opposed outer surface, said inflatable balloon being formed by a layer of a polymeric material extending from the inner surface to the outer surface of the balloon, said outer surface including a knurled bonding surface exterior of an inflatable portion of said balloon, said knurled bonding surface defined by grooves laser ablated into the polymeric material to increase the surface area of said knurled bonding surface by about 50-100% over that of a portion of the outer surface of said balloon having a smooth surface; and
an adhesive for bonding said blade pad bonding surface to said knurled bonding surface of said balloon.

5. A cutting balloon as recited in claim 4 wherein said blade pad bonding surface is formed with a non-smooth surface texture.

6. A cutting balloon as recited in claim 5 wherein said non-smooth surface texture of said blade pad bonding surface is a knurled bonding surface.

7. A cutting balloon as recited in claim 4 wherein said grooves have a groove width in the range of about five microns (5 μm) to about ten microns (10 μm).

8. An incising device comprising:
an inflatable balloon having an inner surface for surrounding an inflation volume and an opposed outer surface, said inflatable balloon being formed by a layer of a polymeric material extending from the inner surface to the outer surface of the balloon, a portion of the outer surface of an inflatable portion of the balloon including a bonding surface defined as a longitudinally aligned strip of the outer surface having a knurled texture defined by a first set of parallel grooves and a second set of parallel grooves aligned at an angle to the first set of parallel grooves laser ablated into the polymeric material; and
an incising element mounted on said outer surface of said balloon, the incising element including a cutting blade partially encapsulated in a blade pad, the blade pad having a bonding surface including a knurled texture defined by a third set of parallel grooves and a fourth set of parallel grooves aligned at an angle to the third set of parallel grooves;
wherein the bonding surface of the blade pad is adhesively bonded to the bonding surface of the outer surface of the inflatable balloon.

* * * * *